(12) United States Patent
Chen et al.

(10) Patent No.: US 7,087,434 B2
(45) Date of Patent: Aug. 8, 2006

(54) AUTOMATIC PORTABLE FORMALDEHYDE ANALYZER

(75) Inventors: James Pey Chen, Schaumburg, IL (US); Paul Drayton, Naperville, IL (US); Jim M. McCarthy, Grayslake, IL (US); Jeffrey A. Panek, Cary, IL (US); John Charles Wagner, La Grange, IL (US)

(73) Assignee: Gas Technology Institute, Des Plaines, IL (US)

( * ) Notice: Subject to any disclaimer, the term of this patent is extended or adjusted under 35 U.S.C. 154(b) by 654 days.

(21) Appl. No.: 10/325,082

(22) Filed: Dec. 20, 2002
(Under 37 CFR 1.47)

(65) Prior Publication Data
US 2004/0121479 A1  Jun. 24, 2004

(51) Int. Cl.
*G01N 33/00* (2006.01)
*G01N 35/00* (2006.01)
*G01N 21/01* (2006.01)

(52) U.S. Cl. .......................... 436/130; 422/62; 422/81; 422/82.05; 422/82.06; 422/82.07; 422/82.08; 422/82.09; 422/83; 422/86; 422/88; 422/91; 436/22; 436/24; 436/43; 436/52; 436/128; 436/166; 436/167; 436/168; 436/172; 436/174; 436/178; 436/181

(58) Field of Classification Search .................. 422/62, 422/81, 82.05–82.09, 83, 86, 88, 91; 436/20–24, 436/43, 52, 127–128, 130, 164, 166–168, 436/172, 174, 178, 181
See application file for complete search history.

(56) References Cited

U.S. PATENT DOCUMENTS

| | | | | |
|---|---|---|---|---|
| 3,985,017 A | * | 10/1976 | Goldsmith ................... | 436/116 |
| 4,198,208 A | * | 4/1980 | Lerner et al. ................ | 436/159 |
| 4,438,206 A | * | 3/1984 | Nakajima et al. ........... | 436/130 |
| 4,666,859 A | * | 5/1987 | Attar .......................... | 436/130 |
| 4,670,405 A | * | 6/1987 | Stetter et al. ................ | 436/151 |
| 4,786,472 A | * | 11/1988 | McConnell et al. .......... | 422/61 |
| 4,960,496 A | * | 10/1990 | Hoke ........................ | 205/779.5 |
| 5,132,227 A | * | 7/1992 | Kelly .......................... | 436/130 |
| 5,205,988 A | * | 4/1993 | Tanaka et al. ................ | 422/91 |
| 5,286,363 A | * | 2/1994 | Anderson et al. ........... | 204/409 |
| 5,992,214 A | * | 11/1999 | Schlitt ....................... | 73/23.35 |
| 6,085,576 A | * | 7/2000 | Sunshine et al. ........... | 73/29.01 |
| 6,096,267 A | * | 8/2000 | Kishkovich et al. .......... | 422/52 |
| 6,136,608 A | * | 10/2000 | Kawachi et al. ............. | 436/130 |

OTHER PUBLICATIONS

Nash, T., Journal of Scientific Instruments 1961, 38, 480-483.*

(Continued)

*Primary Examiner*—Arlen Soderquist
(74) *Attorney, Agent, or Firm*—Mark E. Fejer

(57) ABSTRACT

An apparatus for measuring the concentration of formaldehyde in an exhaust stream from turbines, internal combustion engines and the like, which apparatus includes a portable housing having a sample gas inlet through which a sample gas for analysis is introduced into the portable housing and an analysis system disposed in the portable housing suitable for analyzing the sample gas for the presence of formaldehyde in the sample gas.

10 Claims, 2 Drawing Sheets

OTHER PUBLICATIONS

Yamate, N. et al, Eisei Shikensho Hokoku 1968, 58-64.*
Matsumura, T. et al, Nippon Kagaku Kaishi 1980, 639-644.*
Bisgaard, P. et al, Analytical Letters 1983, 16, 1457-1468.*
Dong, S. et al, Environmental Science and Technology 1987, 21, 581-588.*
Dasgupta, P. K. et al, Atmospheric Environment 1988, 22, 949-963.*
Fan, Q. et al, Analytical Chemistry 1994, 66, 551-556.*
Rodriguez, I. C. et al, International Journal of Environmental Analytical Chemistry 1995, 61, 331-341.*
Lange, J. et al, Fresenius' Journal of Analytical Chemistry 1996, 356, 385-389.*
Word, D. H. et al, Environmental Conference & Exhibit, Minneapolis, May 5-7, 1997, vol. 1, 353-358; Publisher: TAPPI Press, Atlanta, Ga.*
Woo, C. S. et al, Environmental Science and Technology 1998, 32, 169-176.*
Schlitt, H., Occupational Hygiene 1998, 4, 355-365.*
Komazaki, Y. et al, Analyst 1998, 123, 2343-2349.*
Nakano, N. et al, Journal of Environmental Monitoring 1999, 1, 255-258.*
Li, J. et al, Field Analytical Chemistry and Technology 2001, 5, 2-12.*

* cited by examiner

AUTOMATIC PORTABLE FORMALDEHYDE ANALYZER

BACKGROUND OF THE INVENTION

1. Field of the Invention

This invention relates to analyzers for detecting the presence of formaldehyde in gaseous streams. More particularly, this invention relates to an automatic, portable analyzer for detecting the presence of formaldehyde in gaseous streams such as the exhausts from internal combustion engines used for natural gas compression and electrical power generation, the exhausts from turbines, and the exhausts from motor vehicles. The analyzer provides "near real-time" formaldehyde concentration measurements by completely automating the step wise procedures of the conventional Celanese wet chemistry method (EPA Draft Method 323; NCASI Method CI/SG/Pulp-94.02). In addition, the instrument eliminates the fragile glass components and the redundant sample impinger of the conventional wet chemistry test method while retaining the overall accuracy of the measurement.

2. Description of Related Art

The current state-of-the-art methods, such as the use of Fourier Transform Infrared (FTIR) devices, which use narrow absorption band signatures of species of interest, provide accurate formaldehyde detection. However, the capital cost (the order of $100,000), the extensive maintenance, lack of portability, and the required experience of a well-trained technician and spectroscopist make it unfeasible for periodic compliance monitoring, field application, and practical use.

An alternative known system for analyzing the amount of formaldehyde present in a gaseous stream is a dinitrophenylhydrazine (DNPH) coated sampler with solvent extraction and HPLC analysis. However, the DNPH method requires significant after sampling analysis and, thus, is not practical as a near real-time monitor. In addition, it requires solvent extractions and the use of expensive HPLC instruments. A related system involves the use of DNPH solutions in impingers and analysis of the impinger samples with HPLC analysis (EPA Method 11). However, DNPH solutions can be compromised by reactions with $NO_x$ species, particularly when the DNPH solution is not analyzed immediately.

SUMMARY OF THE INVENTION

Accordingly, it is one object of this invention to provide a portable analyzer suitable for measuring the amount of formaldehyde present in a gaseous stream.

It is another object of this invention to provide a system for measuring the amount of formaldehyde present in a gaseous stream that addresses the shortcomings of conventional methods and systems.

These and other objects of this invention are addressed by an apparatus comprising a portable housing having sample inlet means for conveying a sample for analysis into the portable housing and a system disposed in the portable housing suitable for analyzing the sample for the presence of formaldehyde as well as determining the amount of formaldehyde present in the sample.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
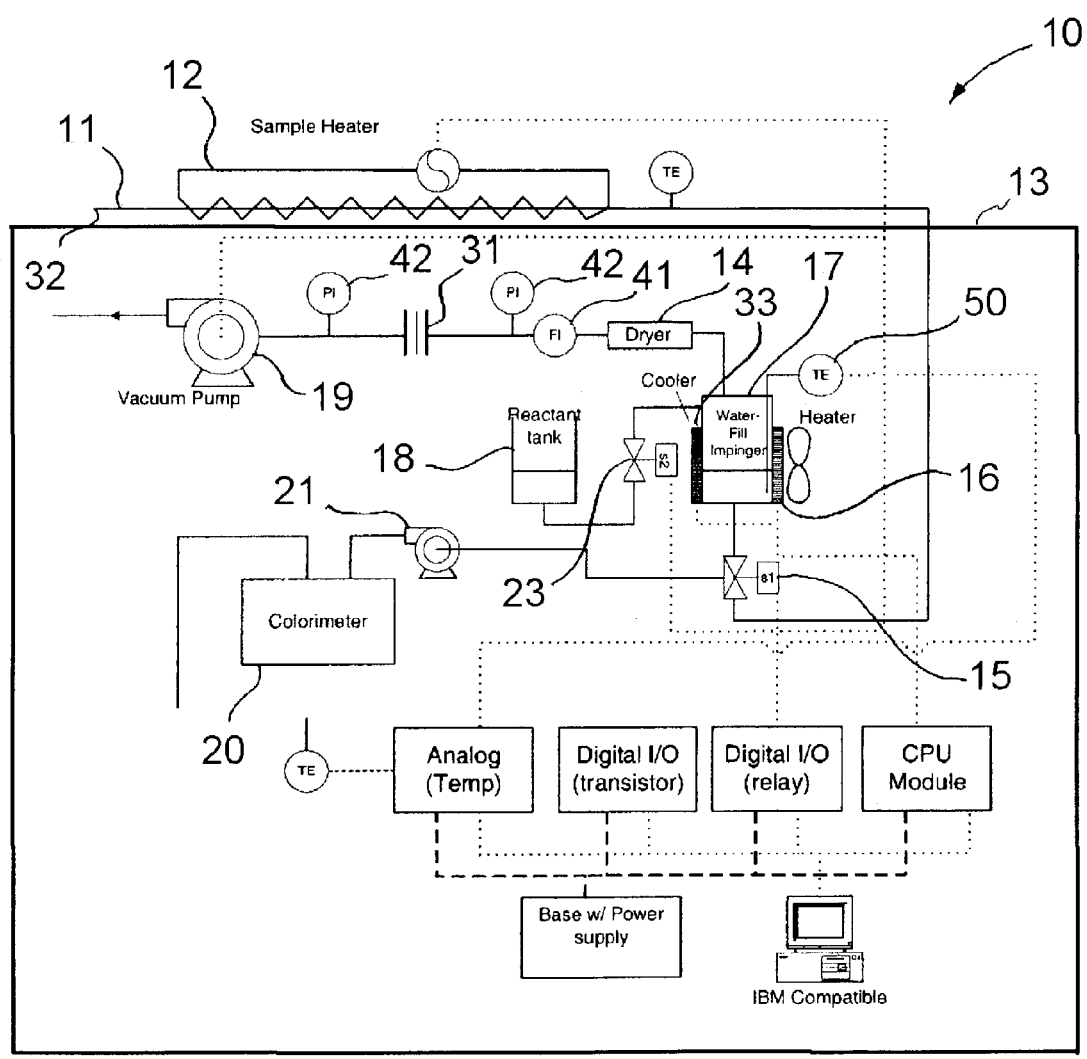
FIG. 1 is a schematic diagram of an automatic, portable formaldehyde analyzer in accordance with one embodiment of this invention.
Figure 2:
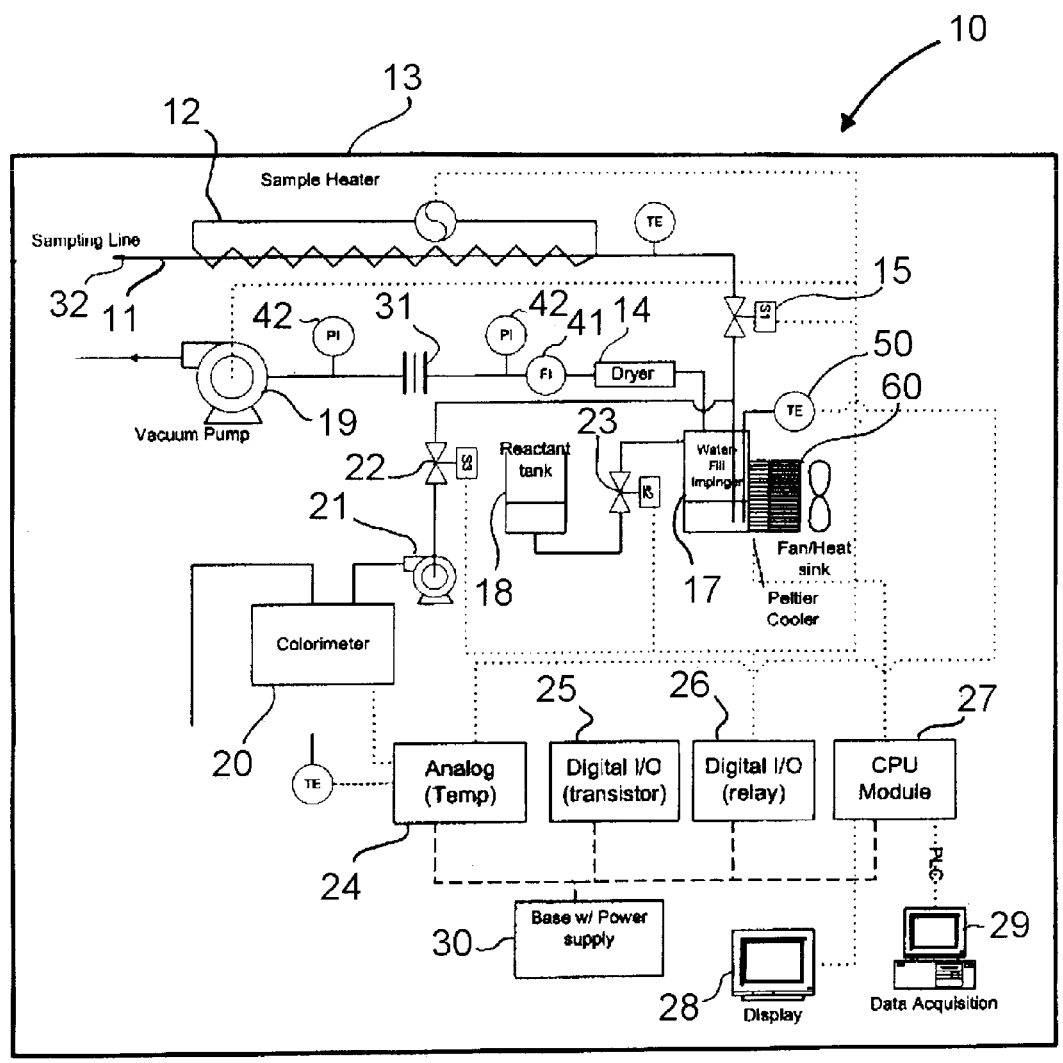
FIG. 2 is a schematic diagram of an automatic, portable formaldehyde analyzer in accordance with another embodiment of this invention.

An automatic portable formaldehyde analyzer in accordance with this invention is shown in FIGS. 1 and 2. This analyzer is suitable for analyzing the formaldehyde concentration in gases exhausted from any known potential source of formaldehyde including, but not limited to, turbines, motor vehicles, and internal combustion engines used for natural gas compression and electrical power generation. It is able to provide near real-time formaldehyde concentration measurements.

The analyzer 10 comprises at least one wall forming a housing 13, a sample conduit 11 having a sample inlet end 32 in fluid communication with a sample source (not shown) and a sample heater 12 arranged to heat a sample in sample conduit 11. In accordance with one embodiment of this invention as shown in FIG. 2, sample conduit 11 and sample heater 12 are disposed within housing 13. Because formaldehyde is soluble in water, sample heater 12 is provided to eliminate water condensation in sample conduit 11. Sample heater 12 may be any heater, for example a heating tape disposed around sample conduit 11, known to those skilled in the art that is suitable for heating the sample in sample conduit 11.

A water-filled impinger 17 is disposed within housing 13 and comprises an impinger sample inlet in fluid communication with sample conduit 11. Water-filled impinger 17 is disposed downstream of sample heater 12. As used herein, the term "downstream" is defined by the direction of flow of the sample for testing as it passes through the analyzer. Cooling means 33 are provided in housing 13 in thermal communication with water-filled impinger 17 for cooling water-filled impinger 17. Heating means 16 are also provided in housing 13 in thermal communication with water-filled impinger 17 for heating water-filled impinger 17. In accordance with one preferred embodiment of this invention as shown in FIG. 2, cooling means 33 and heating means 16 are embodied as a Peltier cooler 60 which is capable of operating in either a heating mode or a cooling mode. It will, however, be apparent to those skilled in the art that the cooling means 33 and heating means 16 may be embodied as individual units within housing 13 as shown in FIG. 1. A reactant container 18 is disposed within housing 13 and includes a reactant outlet in fluid communication with water-filled impinger 17. Sensing means are provided, also within housing 13, for sensing the pressure and flow rate of the sample being analyzed as it passes through the analyzer. Dryer 14 is disposed within housing 13 downstream of water-filled impinger 17 and is provided for the purpose of removing moisture from the gases passing therethrough. Colorimeter 20 comprising a modified sample inlet in fluid communication with water-filled impinger 17 is disposed within housing 17. A vacuum pump 19 comprises a sample inlet in fluid communication with water-filled impinger 17. Vacuum pump 19 is adapted to draw the sample into and through water-filled impinger 17. As discussed in more detail herein below, the analyzer of this invention includes valve means for controlling the sample flow rate through the analyzer.

In operation, a sample gas to be tested is drawn into sample conduit 11, which is heated to prevent water condensation in the sample conduit. The drawn sample gas is then flowed through water-filled impinger 17, which contains an amount of deionized water, for example about 20 ml, in which formaldehyde from the sample gas is accumulated. The water-filled impinger 17 is cooled by cooling means 33 to a temperature in the range of about 0° C. to about 5° C., resulting in cooling of the sample gas. The cooled sample gas is subsequently drawn through a dryer or moisture trap 14, flow rate measuring device 41, pressure indicator 42, critical orifice 31 and vacuum pump 19, all of which are disposed in housing 13. The sample gas is drawn through the water-filled impinger 17 for a period of time sufficient to raise the concentration of formaldehyde in the deionized water to a level that can be detected by a commercially available colorimeter/spectrophotometer. This period of time is typically at least about 15 minutes. Thereafter, vacuum pump 19 is turned off and acetylacetone reagent is introduced from reactant tank 18 into water-filled impinger 17 for mixing with the formaldehyde containing water in water-filled impinger 17. This mixture is then heated by heating means 16 up to a temperature of about 60° C. and held for a period of time, for example about 10 minutes, and then cooled down to room temperature. All temperature sequences and valve on-off timings are controlled, for example, through PLC circuits and PID controllers. A small amount of the processed mixture is then conveyed into the calorimeter 20 by means of pump 21 for analysis. The resulting data is then collected through a data acquisition system 29 and displayed, for example, on display panel 28.

EXAMPLE

This example describes the details of the operation of the apparatus of this invention. Referring to FIG. 1, a sample gas to be analyzed is drawn through sample gas inlet 32 into sample gas conduit 11, which is heated by sample gas heater 12. In this mode of operation, vacuum pump 19 is on and solenoid valve 15 is open. The temperature of the deionized water in water-filled impinger 17 is monitored by temperature sensor 50 until it reaches the desired temperature of 4° C. Once the deionized water has reached the desired temperature and sample gas has been drawn through the deionized water for about 15 minutes, sample gas heater 12 is turned off and solenoid valve 15 closed. Solenoid valve 23, which is disposed between reactant tank 18 and water-filled impinger 17 is then opened, resulting in reactant from reactant tank 18 being drawn into water-filled impinger 17. Vacuum pump 19 is then turned off and solenoid valve 23 is closed. The water/reactant mixture in water-filled impinger 17 is then heated by heating means 16 until it reaches a temperature of about 60° C. as measured by temperature sensor 50 and maintained at this temperature for about 10 minutes. Thereafter, heating means 16 is turned off and cooler 33 turned on. The water/reactant mixture is then cooled to a temperature within about 1° C. of room temperature after which cooler 33 is turned off. Colorimeter 20 is then activated and a portion of the water/reactant mixture from water-filled impinger 17, about 4 ml, is drawn by means of pump 21 into calorimeter 20 in which it undergoes analysis for the presence and concentration of formaldehyde. The output of calorimeter 20 is correlated to the formaldehyde concentration of the sample gas and displayed at display 28.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of this invention.

We claim:

1. An automatic sampling apparatus comprising:
a portable housing comprising sample gas inlet means for conveying a sample gas for analysis into said portable housing; and
an analysis system disposed in said portable housing suitable for analyzing said sample gas for at least one of a presence and a concentration of formaldehyde in said sample gas, said analysis system comprising a sample gas conduit having a sample gas inlet end in fluid communication with said sample gas inlet means, a sample gas heater arranged to heat said sample gas in said sample gas conduit, a water-filled impinger having an impinger sample gas inlet in fluid communication with said sample gas conduit disposed downstream of said sample gas heater, cooling means for cooling said water-filled impinger, heating means for heating said water-filled impinger, a reactant container having a reactant outlet in fluid communication with said water-filled impinger, sensing means for sensing pressure and flow rate of said sample gas, dryer means for removing moisture from said sample gas disposed downstream of said water-filled impinger, a formaldehyde analyzer having a sample inlet in fluid communication with said water-filled impinger, a vacuum pump in fluid communication with said water-filled impinger and adapted to draw said sample gas through said analysis system, and valve means for controlling sample gas flow rates through said analysis system.

2. An apparatus in accordance with claim 1 further comprising a data acquisition system operably connected to said analysis system.

3. An apparatus in accordance with claim 1 wherein said heating means for heating said water-filled impinger and said cooling means for cooling said water-filled impinger are embodied as a single device.

4. An apparatus in accordance with claim 1 wherein said heating means for heating said water-filled impinger and said cooling means for cooling said water-filled impinger are embodied as separate devices.

5. An apparatus in accordance with claim 1, wherein said formaldehyde analyzer is a colorimeter.

6. In an automatic, portable formaldehyde analyzer, a method for determining at least one of a presence and a concentration of formaldehyde in a gaseous stream comprising the steps of:
drawing a sample gas to be analyzed through a sample gas inlet of said analyzer into a sample gas conduit;
heating said sample gas in said sample gas conduit, forming a heated sample gas;
cooling deionized water disposed in a water-filled impinger disposed within a housing of said analyzer and conveying said heated sample gas into said water-filled impinger;
introducing a reactant from a reactant tank disposed within said housing into said water filled impinger, forming a water/reactant mixture;
heating said water/reactant mixture to an elevated temperature, forming a heated water/reactant mixture;

cooling said heated water/reactant mixture to about room temperature, forming a cooled water/reactant mixture;

introducing said cooled water/reactant mixture into a formaldehyde analyzer disposed within said housing; and analyzing said water/reactant mixture for at least one of a presence and a concentration of formaldehyde in said water/reactant mixture.

7. A method in accordance with claim 6, wherein said deionized water is cooled to a temperature of less than about 10° C.

8. A method in accordance with claim 7, wherein said deionized water is cooled to a temperature of about 4° C.

9. A method in accordance with claim 6, wherein said heated water/reactant mixture is maintained at said elevated temperature for at least about 10 minutes.

10. A method in accordance with claim 6, wherein said elevated temperature is in the range of about 50° C. to about 70° C.

* * * * *